(12) United States Patent
Fasolino et al.

(10) Patent No.: US 10,167,155 B2
(45) Date of Patent: Jan. 1, 2019

(54) FIXTURE TO SUPPORT REEL-TO-REEL INSPECTION OF SEMICONDUCTOR DEVICES OR OTHER COMPONENTS

(71) Applicant: Raytheon Company, Waltham, MA (US)

(72) Inventors: Stephen T. Fasolino, McKinney, TX (US); Jason L. Wheeler, Murphy, TX (US); Joshua Ng, Parker, TX (US)

(73) Assignee: Raytheon Company, Waltham, MA (US)

( * ) Notice: Subject to any disclaimer, the term of this patent is extended or adjusted under 35 U.S.C. 154(b) by 267 days.

(21) Appl. No.: 14/822,723

(22) Filed: Aug. 10, 2015

(65) Prior Publication Data

US 2017/0043970 A1 Feb. 16, 2017

(51) Int. Cl.
*B65H 18/10* (2006.01)
*G01N 23/04* (2018.01)
*G01V 5/00* (2006.01)
*G01N 23/20025* (2018.01)

(52) U.S. Cl.
CPC ........... *B65H 18/103* (2013.01); *G01N 23/04* (2013.01); *G01N 23/20025* (2013.01); *G01V 5/00* (2013.01); *G01N 2223/6113* (2013.01); *G01N 2223/6116* (2013.01); *G01N 2223/643* (2013.01)

(58) Field of Classification Search
CPC .................. B65H 18/103; G01N 23/20025
See application file for complete search history.

(56) References Cited

U.S. PATENT DOCUMENTS

| | | | | | |
|---|---|---|---|---|---|
| 5,460,335 | A | * | 10/1995 | Jin | B65H 18/103 242/355 |
| 5,489,071 | A | * | 2/1996 | Tarpley, Jr. | G11B 15/093 242/333.7 |
| 6,073,342 | A | * | 6/2000 | Asai | H05K 13/0061 198/586 |

(Continued)

FOREIGN PATENT DOCUMENTS

| | | | |
|---|---|---|---|
| JP | 2003297274 A | * | 10/2003 |
| WO | WO 00/58718 | | 10/2000 |

OTHER PUBLICATIONS

English Translation of JP 2003297274.*

(Continued)

*Primary Examiner* — David J Makiya
*Assistant Examiner* — Soorena Kefayati

(57) ABSTRACT

A system includes a component inspection system having a radiation source configured to generate radiation and a radiation detector configured to detect the radiation after the radiation passes through components to be inspected. The system also includes a fixture configured to receive multiple reels that are each configured to receive a tape in or on which the components are located. The fixture includes a base configured to be secured to a support, a shaft, one or more motors mounted to the shaft and configured to rotate the reels, and one or more joints coupling the shaft and base. The one or more joints are configured to allow (i) rotation of the shaft about a longitudinal axis of the shaft to change an orientation of the shaft with respect to the base and (ii) rotation of the shaft to change a direction at which the shaft extends away from the base.

23 Claims, 9 Drawing Sheets

(56) References Cited

U.S. PATENT DOCUMENTS

| | | | | |
|---|---|---|---|---|
| 6,892,976 | B2* | 5/2005 | Foo | B65H 18/026 |
| | | | | 156/184 |
| 7,150,572 | B2* | 12/2006 | McNestry | B41J 2/325 |
| | | | | 400/223 |
| 7,627,083 | B2 | 12/2009 | Ross et al. | |
| 7,684,608 | B2* | 3/2010 | Chen | G01R 31/2893 |
| | | | | 382/103 |
| 7,711,088 | B2 | 5/2010 | Gibson et al. | |
| 7,854,551 | B2* | 12/2010 | Lv | A61B 6/447 |
| | | | | 378/189 |
| 8,516,739 | B2* | 8/2013 | White | A01K 97/01 |
| | | | | 43/19.2 |
| 8,647,705 | B2 | 2/2014 | Reeves et al. | |
| 8,767,912 | B1 | 7/2014 | Alzaidi | |
| 9,419,549 | B2* | 8/2016 | Yim | H02P 27/08 |
| 2007/0262188 | A1* | 11/2007 | Kubota | B65H 75/28 |
| | | | | 242/532.2 |
| 2008/0219743 | A1* | 9/2008 | McNestry | B41J 33/34 |
| | | | | 400/234 |
| 2013/0022167 | A1* | 1/2013 | Cardoso | G01N 23/2206 |
| | | | | 378/46 |
| 2017/0079871 | A1* | 3/2017 | Zhang | A61H 23/004 |

OTHER PUBLICATIONS

"TruView Prime X-Ray Inspection System" Creative Electron, Inc. http://creativeelectron.com/truview-prime/ 2015, 8 pgs.

"Find Counterfeit Components: TruView X-Ray Reel-to-Reel" Creative Electron, Inc. http://creataiveelectron.com/find-counterfeit-components-truview-X-ray-reel-reel/ 2015, 5 pgs.

"RTX-113 A unique X-Ray inspection system by Glenbrook Technologies," Inc. http://www.glenbrooktech.com/Reel-toReel.php 2015, 4 pgs.

"Reel to Reel X-ray Inspection for Counterfeit Electronic Components," https://www.youtube.com/watch?v=BiWpAlFgiMA, Jan. 20, 2011.

"Glenbrook fully automated reel to reel electronic component inspection," https://www.youtube.com/watch?v=g5TfrUc_ac0, May 4, 2011.

Notification of Transmittal of the International Search Report and the Written Opinion of the International Searching Authority, or the Declaration dated Aug. 30, 2016 in connection with International Patent Application No. PCT/US2016/037052.

E. E. Chaban et al., "Two-axis sample positioning mechanism", Rev. Sci. Instrum., vol. 47, No. 7, Jul. 1, 1978, p. 828-831.

* cited by examiner

FIXTURE TO SUPPORT REEL-TO-REEL INSPECTION OF SEMICONDUCTOR DEVICES OR OTHER COMPONENTS

TECHNICAL FIELD

This disclosure is generally directed to the inspection of semiconductor devices or other components. More specifically, this disclosure is directed to a fixture that supports reel-to-reel inspection of semiconductor devices or other components.

BACKGROUND

A growing problem worldwide involves counterfeit electronic components, such as counterfeit integrated circuit chips or other semiconductor devices. Various inspection systems have been developed to try to combat this problem. For example, some inspection systems X-ray electronic components and determine whether the resulting X-ray images indicate that the electronic components are genuine or counterfeit.

Conventional inspection systems often suffer from various problems. For example, some conventional systems require operators to manually place electronic components onto trays, place the trays into inspection systems, and perform the same task repeatedly. These approaches are often costly and time-consuming and create wear-and-tear on the inspection systems by requiring constant opening and closing of doors, using servo motors to position electronic components, and powering inspection systems on and off. Moreover, these approaches often increase the risk of operators inadvertently damaging electronic components (such as via electrostatic discharges) and provide ergonomically poor environments for the operators.

In a reel-to-reel inspection system, electronic components are stored on or in a tape that is wound around a first reel. The tape can be unwound from the first reel, the electronic components can be examined, and the tape can be wound around a second reel. This can help to resolve various problems encountered using other types of inspection systems. However, there is currently no simple way to add reel-to-reel inspection capabilities to existing non-reel-to-reel inspection systems. Rather, an entirely new inspection system would typically need to be purchased.

SUMMARY

This disclosure provides a fixture that supports reel-to-reel inspection of semiconductor devices or other components.

In a first embodiment, an apparatus includes a fixture configured to receive multiple reels that are each configured to receive a tape in or on which components to be inspected are located. The fixture includes a base configured to be secured to a support, a shaft, and one or more motors mounted to the shaft and configured to rotate the reels. The fixture also includes one or more joints coupling the shaft and the base, where the one or more joints are configured to allow (i) rotation of the shaft about a longitudinal axis of the shaft to change an orientation of the shaft with respect to the base and (ii) rotation of the shaft to change a direction at which the shaft extends away from the base.

In a second embodiment, a system includes a component inspection system having a radiation source configured to generate radiation and a radiation detector configured to detect the radiation after the radiation passes through components to be inspected. The system also includes a fixture configured to receive multiple reels that are each configured to receive a tape in or on which the components are located. The fixture includes a base configured to be secured to a support, a shaft, and one or more motors mounted to the shaft and configured to rotate the reels. The fixture also includes one or more joints coupling the shaft and the base, where the one or more joints are configured to allow (i) rotation of the shaft about a longitudinal axis of the shaft to change an orientation of the shaft with respect to the base and (ii) rotation of the shaft to change a direction at which the shaft extends away from the base.

In a third embodiment, a method includes securing a base of a fixture to a support. The method also includes placing a shaft of the fixture into a specified location, where one or more joints couple the shaft and the base and one or more motors are mounted to the shaft. The method further includes coupling multiple reels to the one or more motors, where each reel is configured to receive a tape in or on which components to be inspected are located. In addition, the method includes controlling winding and unwinding of the tape from the reels to allow a component inspection system to capture one or more images of each component. The one or more joints are configured to allow (i) rotation of the shaft about a longitudinal axis of the shaft to change an orientation of the shaft with respect to the base and (ii) rotation of the shaft to change a direction at which the shaft extends away from the base.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 9, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

Figure 1:
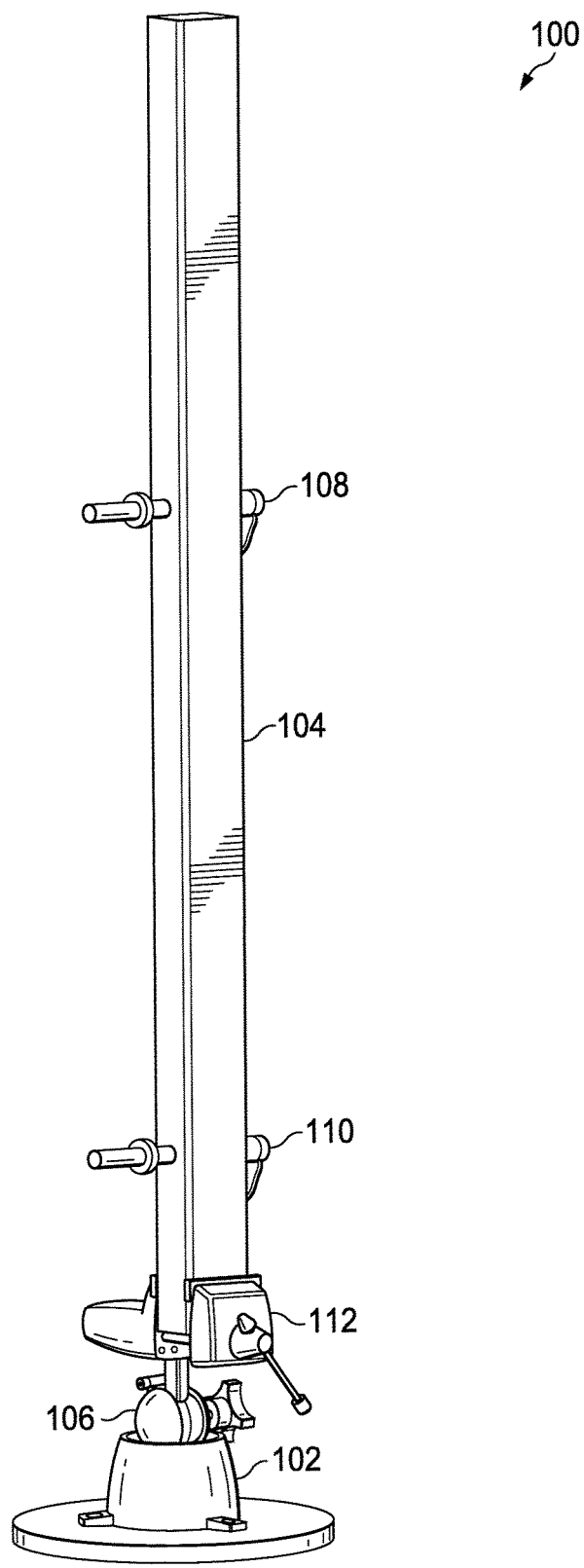
FIG. 1 illustrates an example fixture that supports reel-to-reel inspection of semiconductor devices or other components in accordance with this disclosure.

FIG. 1 illustrates an example fixture 100 that supports reel-to-reel inspection of semiconductor devices or other components in accordance with this disclosure. As described in more detail below, the fixture 100 is designed to provide a reel-to-reel inspection capability within an inspection system not designed for reel-to-reel inspections. The fixture 100 can therefore be said to represent a "drop-in accessory" that can be compatible and used with a wide array of real-time X-ray or other inspection systems, including inspection systems produced by a number of different manufacturers.

As shown in FIG. 1, the fixture 100 includes a base 102, a shaft 104, and a pivot joint 106. The base 102 generally denotes a portion of the fixture 100 that can be secured to a support structure in order to hold the fixture 100 in place. For example, the base 102 could be secured to a structure within or adjacent to an inspection system so that the shaft 104 can be placed into a suitable location for use during the inspection of semiconductor devices or other components.

The base 102 can be formed from any suitable material(s) and in any suitable manner. For instance, the base 102 could be formed from one or more metals, and the base 102 could be formed using machining or molding operations. The base 102 could also have any suitable size, shape, and dimensions. In this example, the base 102 has a generally circular cross-section that narrows near the top of the base 102, although this is for illustration only. In addition, the bottom of the base 102 is shown as having various projections that can be secured to another structure, such as by using bolts. However, any other suitable coupling mechanism(s) could be used.

The shaft 104 extends away from the base 102. The shaft 104 generally denotes a structure on which other components of the fixture 100, such as two motors 108-110, can be mounted. As described in more detail below, the motors 108-110 include axles or other projections on which two reels can be mounted. A first of the reels can hold semiconductor devices or other components encapsulated within or otherwise held by a tape, and the tape can be extended to a second of the reels. By controlling operation of the motors 108-110, the tape can be unwound from the first reel, inspected, and collected on the second reel. The tape can also be unwound from the second reel, optionally inspected again, and wound back on the first reel. This can help to facilitate inspection of the components from one or multiple angles.

The shaft 104 can be formed from any suitable material(s) and in any suitable manner. For instance, the shaft 104 could be formed from one or more metals, and the shaft 104 could be formed using machining or molding operations. The shaft 104 could also have any suitable size, shape, and dimensions. In this example, the shaft 104 has a generally square or rectangular cross-section with rounded corners, although this is for illustration only. In addition, the shaft 104 could have any suitable length as well as support any suitable separation between the motors 108-110. In this example, the motors 108-110 are in fixed positions and have axles that extend through the shaft 104, although the motors 108-110 could have adjustable positions and may or may not have axles that extend through the shaft 104.

Each motor 108-110 includes any suitable structure configured to receive and rotate a reel. For example, each motor 108-110 could represent a direct current (DC) motor. In some embodiments, each motor 108-110 could rotate in response to pulses in an input voltage or other input signal. Through suitable control of the input signals, the motors 108-110 could be driven to rotate in fixed steps (such as fixed partial revolutions) or to rotate continuously. Moreover, the motors 108-110 can be configured to rotate in different directions, such as when the motor 110 rotates in one direction to support "forward" winding of tape between the reels and the motor 108 rotates in the opposite direction to support "backward" winding of the tape between the reels. Note, however, that other embodiments could also be used. For instance, a single motor could be used to drive both reels.

The pivot joint 106 allows the position and orientation of the shaft 104 to vary with respect to the base 102. For example, the pivot joint 106 allows the shaft 104 to rotate about the longitudinal axis of the shaft 104. As described below, this could allow components to be inspected from multiple angles. As a particular example, an inspection system could capture top-down or bottom-up images of the components being inspected when the shaft 104 is in one orientation, and the shaft 104 can be rotated about its axis to allow the inspection system to capture side or oblique images of the components. The pivot joint 106 also allows the entire shaft 104 to be rotated so that the shaft 104 is pointing in a different direction. For example, the pivot joint 106 could be rotated downward 90° in FIG. 1 so that the shaft 104 extends horizontally away from the base 102 instead of vertically. As described below, this could allow the fixture 100 to be used with inspection systems having different configurations.

The pivot joint 106 denotes any suitable structure allowing pivoting or rotation of a portion of a fixture. In this example, the pivot joint 106 includes a ball joint and a handle connected to a threaded bolt extending partially through the ball joint. However, the pivot joint 106 could be implemented in any other suitable manner. Also, while the use of a single joint 106 is shown here, multiple joints could also be used. For instance, a ball or other first joint could allow rotation of the shaft 104 about its longitudinal axis, while an elbow or other second joint could allow rotation of the entire shaft 104. In addition, in this example, the shaft 104 is secured to the pivot joint 106 using a vice 112, which allows the shaft 104 to be quickly and easily removed from the pivot joint 106. However, other mechanisms could be used to removably couple the shaft 104 and the pivot joint 106, or the shaft 104 and the pivot joint 106 could be permanently attached or integrated.

The fixture 100 provides a convenient way to add reel-to-reel inspection capabilities to new or existing inspection systems. This can provide various advantages depending on the implementation. For example, the use of the fixture 100 to provide reel-to-reel inspection capabilities can drastically reduce the amount of time and associated costs for inspecting a large number of semiconductor devices or other components. Also, the use of the fixture 100 to provide reel-to-reel inspection capabilities can reduce wear-and-tear on an inspection system, such as by reducing the number of times a chamber door is opened and closed, reducing the use of servo motors in the inspection system, and reducing the number of power cycles. Further, the use of the fixture 100 to provide reel-to-reel inspection capabilities can reduce or eliminate handling artifacts associated with manual manipulation of semiconductor devices or other components (such as physical damage or contamination), reduce or eliminate the need to manually re-reel components after inspection, and reduce or minimize exposure to electrostatic discharge events. Moreover, the use of the fixture 100 to provide reel-to-reel inspection capabilities can provide improved ergonomics and reduce or eliminate repetitive motions related to sample preparation, which helps to improve the operator environment. These benefits can be obtained without requiring the purchase of an entirely new inspection system designed specifically for reel-to-reel inspections. In addition, the shaft 104 could be manually or electronically repositioned or reoriented, such as by using a motor or other electronic actuator. If electronically operated, an inspection system could automatically control the positioning of the shaft 104 so that, for example, different views of the components being inspected can be captured. This may allow the inspection system to provide real-time multi-directional imaging, which can increase inspection versatility for inspection systems that lack integrated rotational capabilities.

Additional features of the fixture 100, as well as details of example systems in which the fixture 100 can be used, are provided below. Note, however, that the fixture 100 could be used in a wide variety of systems and that the following description does not limit the fixture 100 to use with a particular system.

Although FIG. 1 illustrates one example of a fixture 100 that supports reel-to-reel inspection of semiconductor devices or other components, various changes may be made to FIG. 1. For example, the relative sizes, shapes, and dimensions of the components of the fixture 100 are for illustration only.

Figure 2:
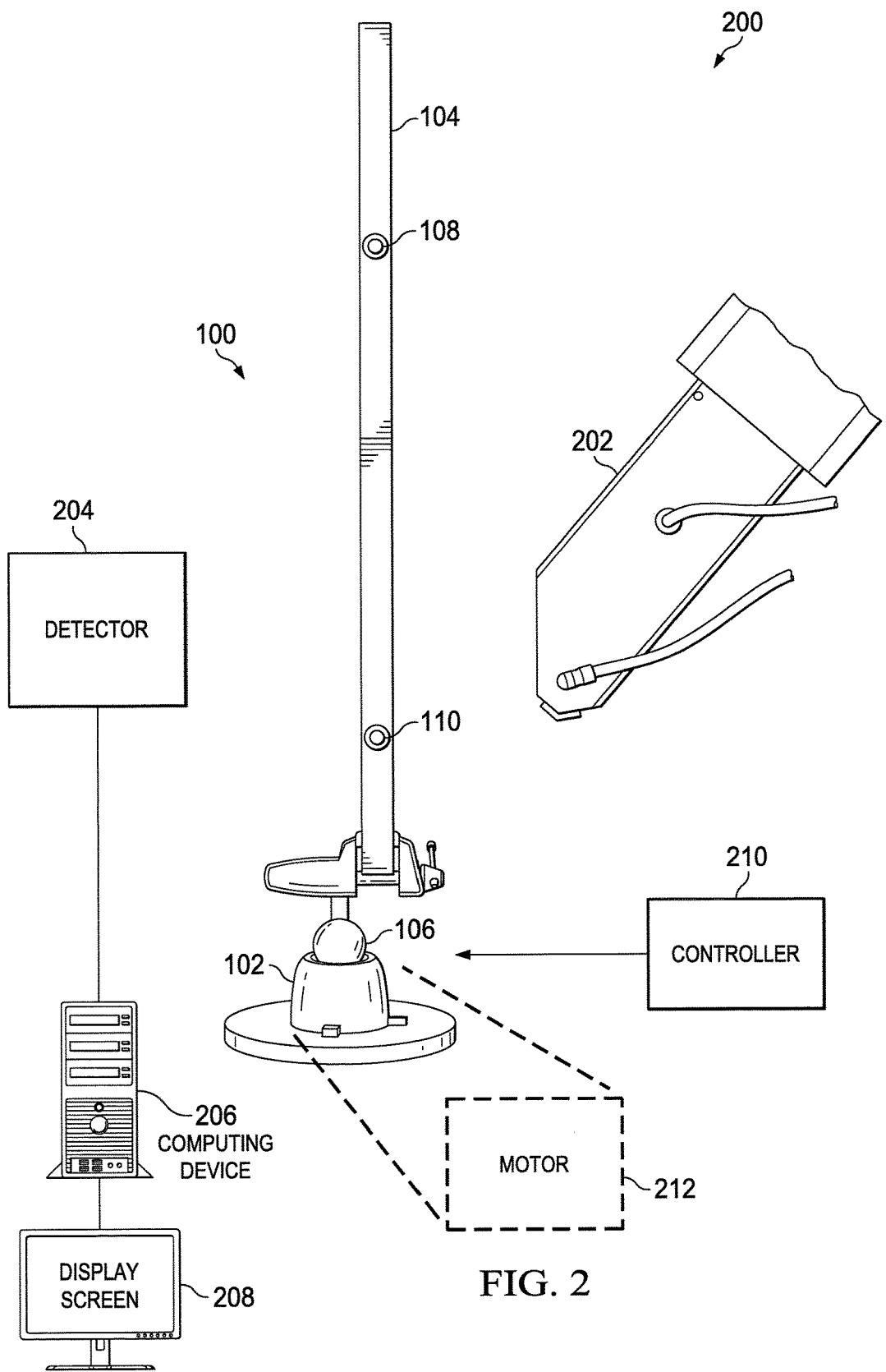
FIGS. 2 through 4 illustrate an example system that supports reel-to-reel inspection of semiconductor devices or other components in accordance with this disclosure.
Figure 3:
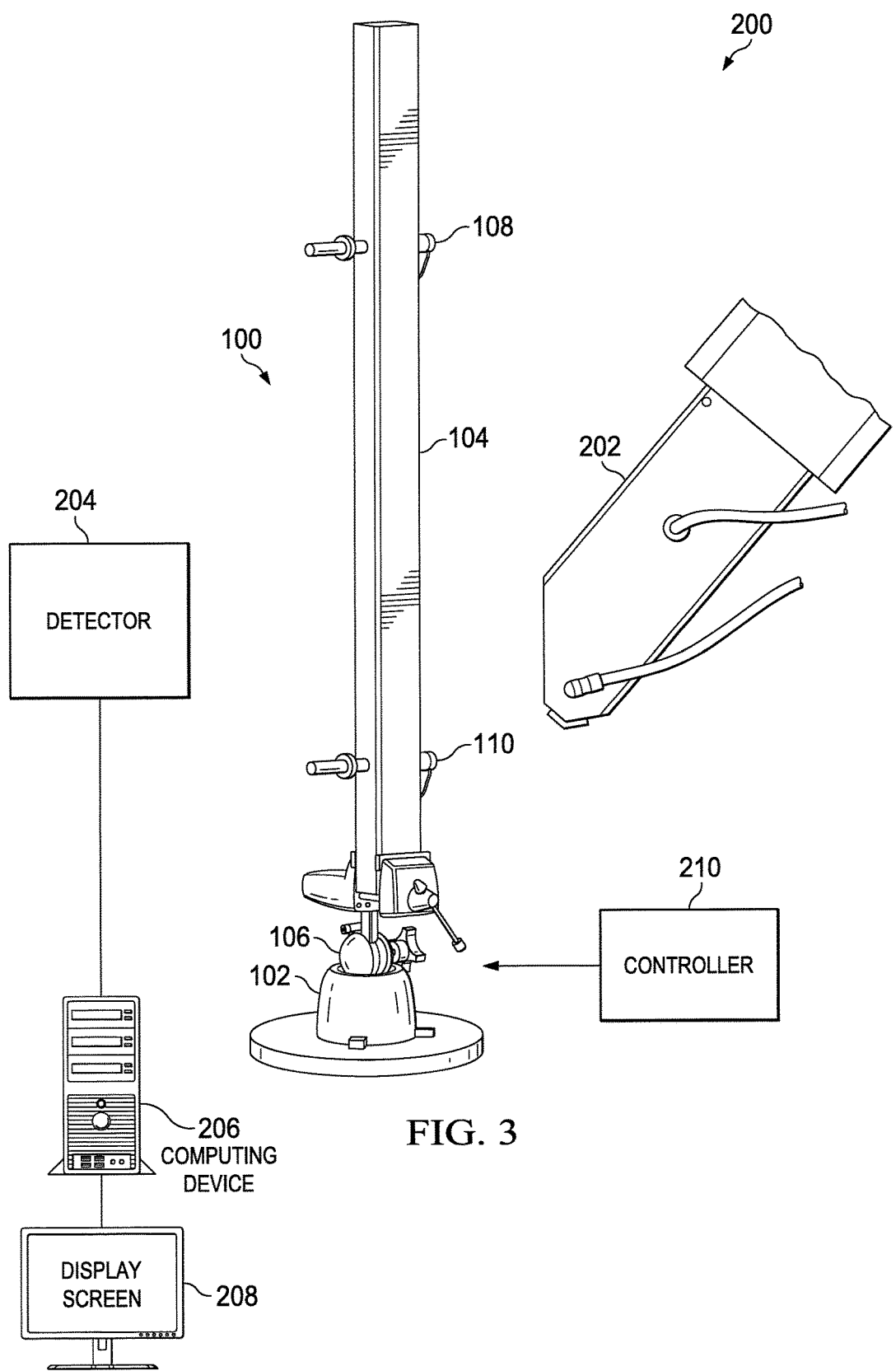
Figure 4:
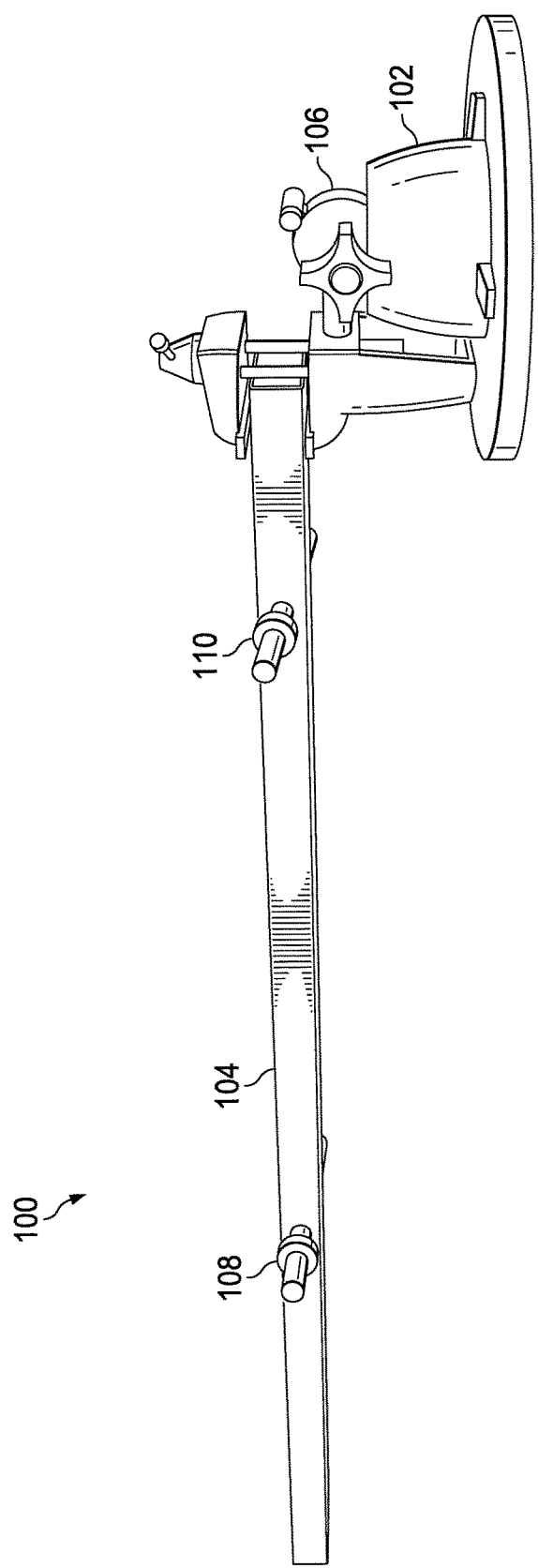

FIGS. 2 through 4 illustrate an example system 200 that supports reel-to-reel inspection of semiconductor devices or other components in accordance with this disclosure. As shown in FIG. 2, the fixture 100 is shown as holding the shaft 104 in the vertical position between an X-ray or other radiation source 202 and an X-ray or other radiation detector 204. During operation, the motors 108-110 hold two reels and operate to move a tape containing semiconductor devices or other components from one reel to another. This positions the components between the radiation source 202 and the radiation detector 204. X-rays or other radiation from the radiation source 202 passes through the components and is captured or measured by the radiation detector 204. The radiation detector 204 can therefore generate X-ray or other images of the components being inspected.

The images generated by the radiation detector 204 can be subjected to one or more analyses. For example, when the components being inspected are integrated circuit chips or other semiconductor devices, the analyses could determine whether each of the semiconductor devices is likely an authentic component or a counterfeit component. Various other types of analyses could be performed using information about the components being inspected generated by the detector 204.

The radiation source 202 includes any suitable structure for generating radiation used to inspect one or more components. For example, the radiation source 202 could denote an X-ray source that generates a suitable amount of X-rays for inspecting the particular components of interest. The radiation detector 204 includes any suitable structure for detecting or measuring radiation used to inspect one or more components. For instance, the radiation detector 204 could denote a digital X-ray detector that generates digital X-ray images of the components being inspected. Note that the form factor of the radiation source 202 is for illustration only and that any other suitable form factor could be used.

In some embodiments, the system 200 includes a computing device 206 and a display screen 208, which may be separate from or integrated with the computing device 206. The computing device 206 could execute logic that receives X-ray or other images from the radiation detector 204 and analyzes the images to identify issues with the components being inspected. The computing device 206 could also display the images on the display device 208, display alerts when counterfeit components or other issues are detected with the components being inspected, or perform other functions. The computing device 206 includes any suitable processing functionality for processing or analyzing images of components being inspected.

A controller 210 can be used in the system 200 to allow an operator to manually control the operation of the motors 108-110. The following represents example functions that could be implemented using the controller 210, although other or additional functions could also be supported. The controller 210 could include pushbuttons or other controls that cause the motors 108-110 to rotate the reels in fixed steps or continuously (such as during scrolling). The controller 210 could also include controls for adjusting how quickly the reels scroll. In addition, the controller 210 could include controls for adjusting the pulse width of control signals to account for (i) the actual pitch or separation of the components within the tape being unwound/wound and (ii) the size(s) of the reel(s). As noted above, when not scrolling, the motors 108-110 could be driven to rotate in fixed steps (such as fixed partial revolutions). The amount of rotation can be controlled based on the width of pulses provided to the motors 108-110. However, the amount of rotation by the motors 108-110 required to move from one component to another component in the tape can vary, such as due to reels of different sizes or different spacings between components within the tape. The controller 210 can allow the operator to modify the width of pulses in control signals provided to the motors 108-110 in order to account for these or other factors.

Note that any other or additional functions could be supported using the controller 210. The controller 210 includes any suitable structure for controlling the operation of one or more motors in order to control the inspection of components. One example implementation of the controller 210 and example functions of the controller 210 are provided below.

At least one motor 212 or other type of actuator could optionally be used within or in conjunction with the fixture 100. As noted above, in some embodiments, the shaft 104 could be electronically repositioned or reoriented. The motor 212 facilitates the repositioning or reorientation of the shaft 104. For example, the motor 212 could be located within the base 102 of the fixture 100 and be used to rotate the shaft 104 about its longitudinal axis and/or rotate the shaft 104 to point in a different direction. Note, however, that the motor 212 could be located in any other suitable position from which the motor can reposition or reorient the shaft 104. A single motor 212 or multiple motors 212 could be used to facilitate the repositioning or reorientation of the shaft 104. Each motor 212 includes any suitable structure for repositioning or reorienting at least a portion of a fixture.

FIG. 3 illustrates rotation of the fixture 100 about a longitudinal axis of the shaft 104. This rotation can be accomplished by rotating the pivot joint 106 while maintaining the shaft 104 in the same direction. This type of rotation of the fixture 100 could be used to support scanning of semiconductor devices or other components from different angles. As a particular example, top or bottom views of the components could be obtained when the tape containing the components is transferred from a first reel to a second reel, and side or oblique views of the components could be obtained when the tape containing the components is transferred from the second reel back to the first reel.

FIG. 4 illustrates rotation of the fixture 100 about the pivot joint 106 itself, causing the shaft 104 to point in a different direction. Among other things, this type of rotation of the fixture 100 could allow the fixture 100 to be used with different types of inspection systems, such as those with vertical, horizontal, and other detector configurations. For example, some inspection systems position an X-ray source and an X-ray detector horizontally with respect to one other, while other inspection systems position an X-ray source and an X-ray detector vertically with respect to one other. Still other inspection systems may have a different arrangement of the X-ray source and the X-ray detector. Allowing the shaft 104 to rotate in this manner facilitates use of the fixture 100 regardless of the positioning of the X-ray source and the X-ray detector.

Figure 5:
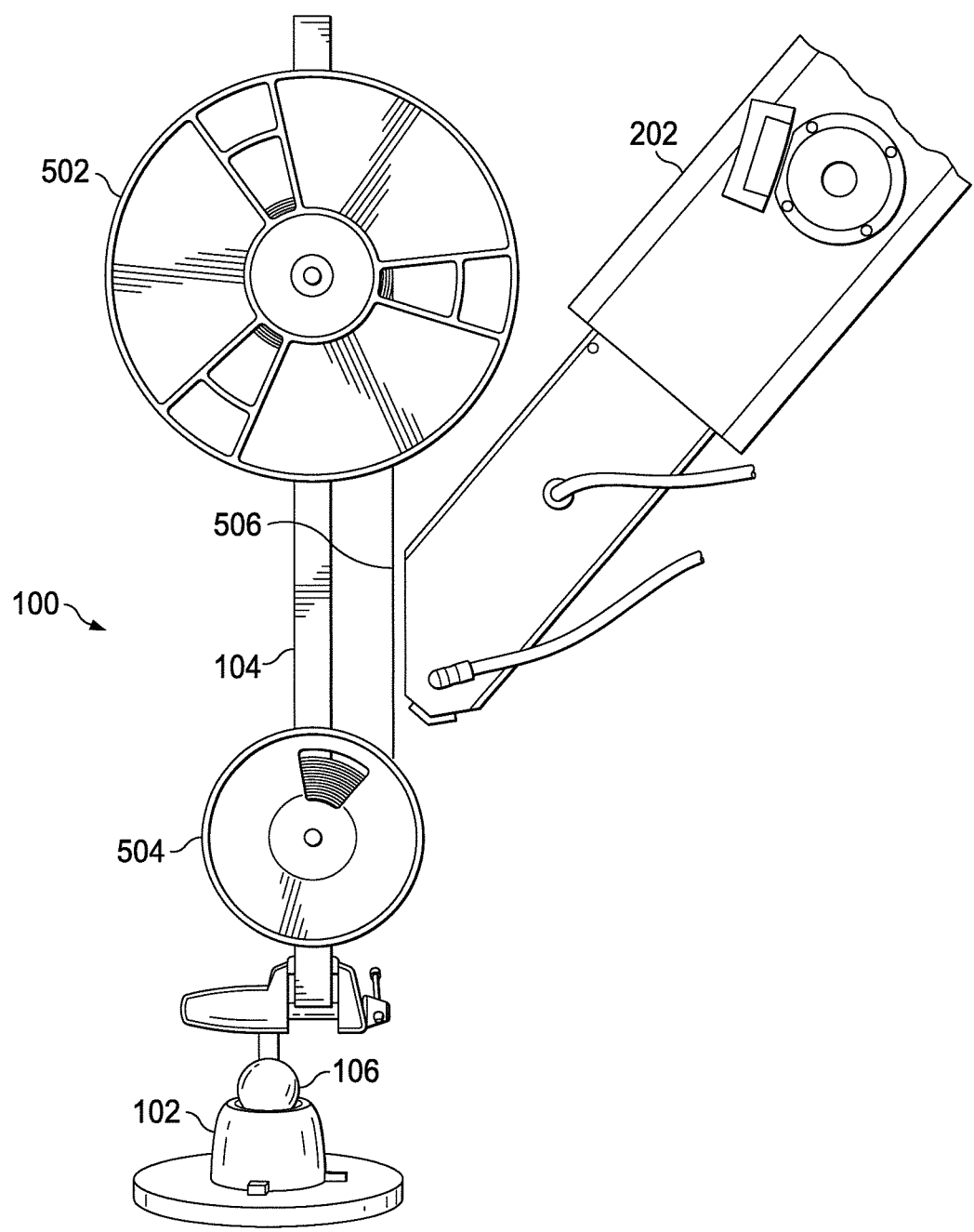
FIGS. 5 through 7 illustrate an example use of a system that supports reel-to-reel inspection of semiconductor devices or other components in accordance with this disclosure.
Figure 6:
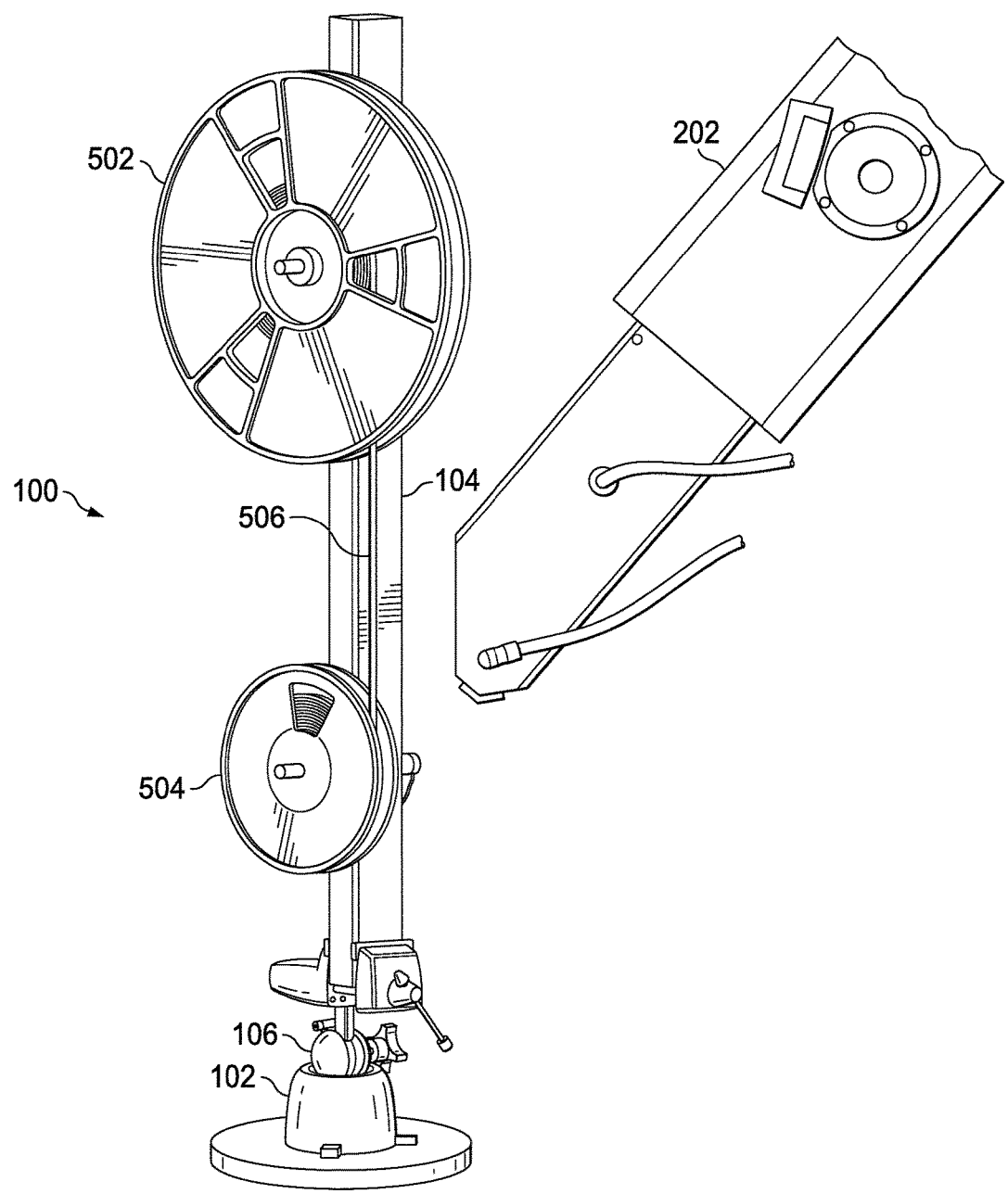
Figure 7:
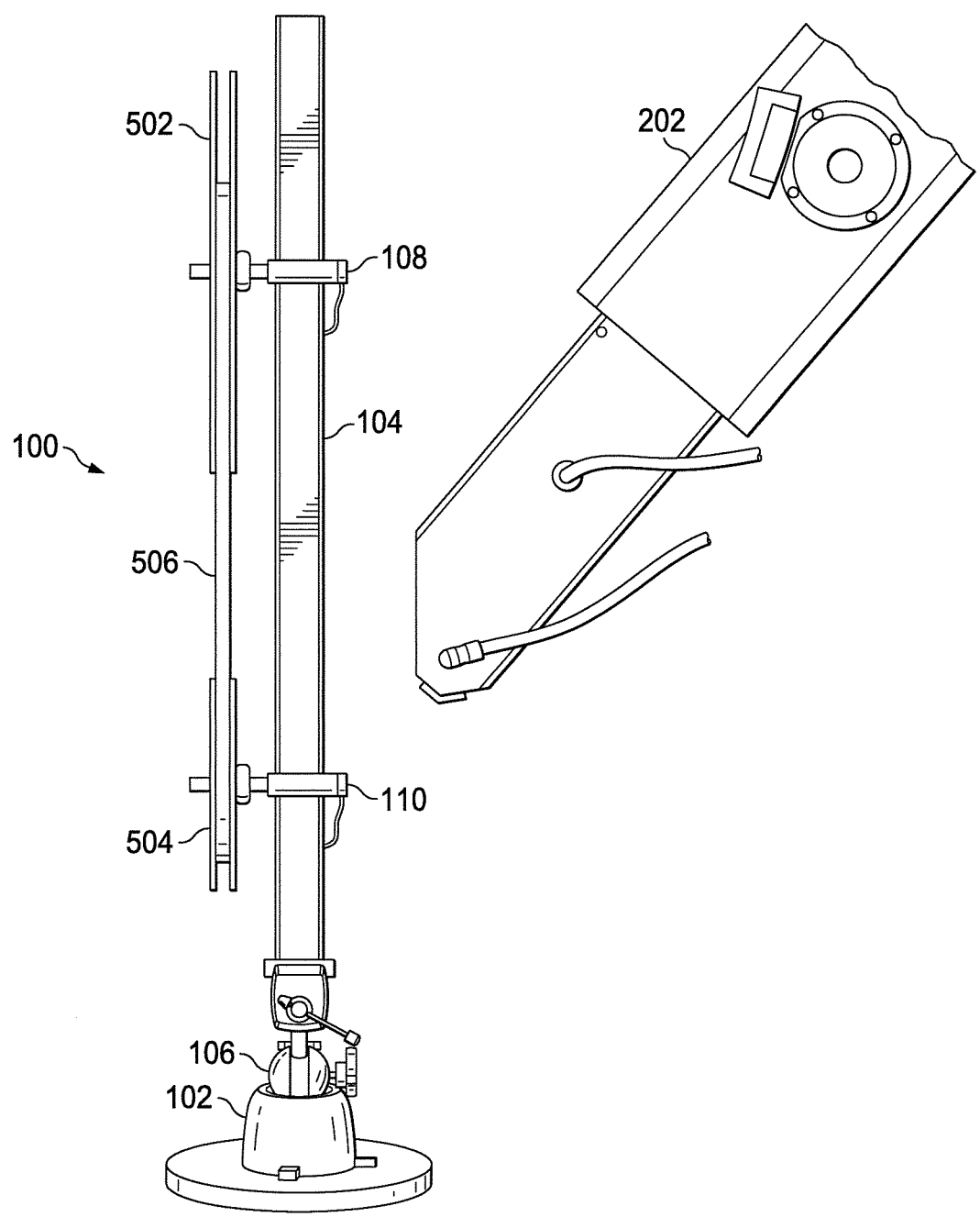

FIGS. 5 through 7 illustrate an example use of the system 200 that supports reel-to-reel inspection of semiconductor devices or other components in accordance with this disclosure. As shown in FIG. 5, a first reel 502 has been attached to the motor 108, and a second reel 504 has been attached to the motor 110. A tape 506 containing semiconductor devices or other components extends between the reels 502-504. The motors 108-110 rotate in order to transfer the tape 506 from one reel to another. In doing so, the components contained on or within the tape 506 pass through an imaging location, which denotes a location where the radiation detector 204 can capture radiation from the radiation source 202 passing through the components.

In FIG. 5, the fixture 100 is configured so that the tape 506 is generally perpendicular to the direction of imaging. Depending on the components and their arrangement in the tape 506, this could allow the system 200 to capture top or bottom views of the components. In FIG. 6, the fixture 100 has been rotated approximately 45° about the longitudinal axis of the shaft 104, and oblique images of the components could be captured. In FIG. 7, the fixture 100 has been rotated approximately 90° about the longitudinal axis of the shaft 104, and side images of the components could be captured. The number of angles and the values of those angles could vary based on, for instance, the components being inspected. Also, the number of times that each component is imaged could vary based on particular needs.

Note that the relative sizes of the reels 502-504 shown in FIGS. 5 through 7 are for illustration only. Each of the reels 502-504 could have any other suitable size, and in some implementations the reels 502-504 could be of equal size. Also note that the design of the fixture 100 here provides obstruction-free imaging paths, which allows the images of the components to be captured from multiple angles. This can help to increase or optimize radiographic imaging quality, such as by providing increased dynamic range or magnification.

Although FIGS. 2 through 4 illustrate one example of a system 200 that supports reel-to-reel inspection of semiconductor devices or other components and FIGS. 5 through 7 illustrate one example use of the system 200, various changes may be made to FIGS. 2 through 7. For example, the fixture 100 could be used with any other suitable inspection system and with any other suitable reels.

Figure 8:
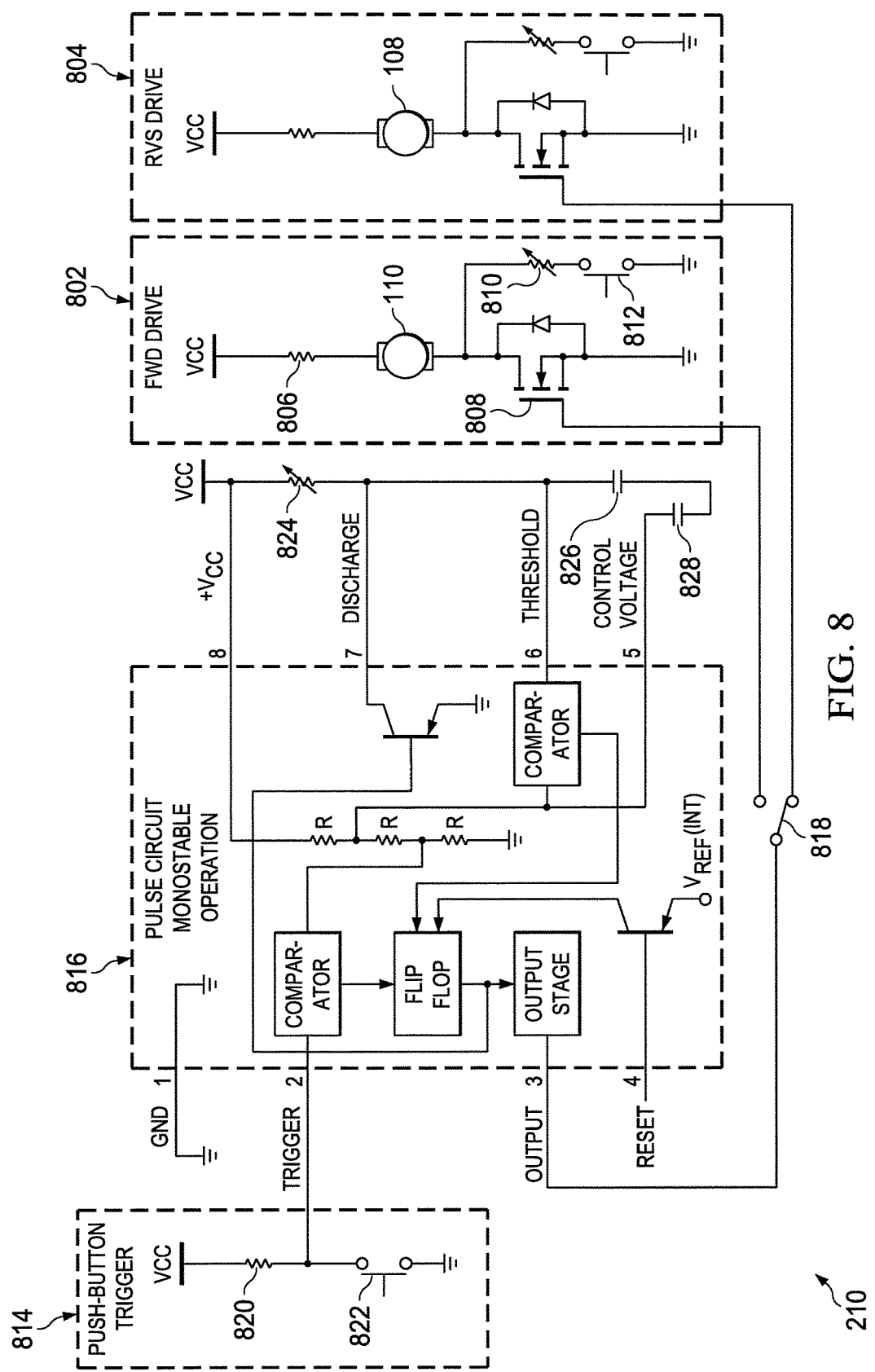
FIG. 8 illustrates an example controller for a system that supports reel-to-reel inspection of semiconductor devices or other components in accordance with this disclosure.

FIG. 8 illustrates an example controller 210 for a system that supports reel-to-reel inspection of semiconductor devices or other components in accordance with this disclosure. For ease of explanation, the controller 210 is described as being used in the system 200 of FIGS. 2 through 7 with the fixture 100 of FIG. 1. However, the controller 210 could be used with any other suitable fixture or any other suitable system.

As shown in FIG. 8, the controller 210 includes a forward drive circuit 802 and a reverse drive circuit 804. The drive circuits 802-804 are used by the controller 210 to control the motors 108-110, which allows the controller 210 to control movement of the tape 506 in different directions. In this example, the forward direction causes the motor 110 to rotate, which unwinds the tape 506 from the reel 502 onto the reel 504. The reverse direction causes the motor 108 to rotate, which unwinds the tape 506 from the reel 504 onto the reel 502. However, the associations of the forward and reverse directions with the motors 108-110 are for illustration only.

Each drive circuit 802-804 includes a resistor 806 that is coupled to one side of the associated motor 108-110. Each drive circuit 802-804 also includes a transistor 808, potentiometer 810, and pushbutton 812 that are coupled to another side of the associated motor 108-110. The transistor 808 provides one path that allows current to flow through the associated motor to ground, while the potentiometer 810 and pushbutton 812 provide another path that allows current to flow through the associated motor to ground. As described below, the transistor 808 can be driven by other components of the controller 210 to cause the motor 108 or 110 to rotate by an amount defined by a pulse in a control signal, which is provided to a gate of the transistor 808. Ideally, this rotation is adequate to advance the tape 506 from one component being inspected to the next component being inspected. The pushbutton 812 can be operated manually to cause the motor 108-110 to rotate. The pushbutton 812 could be used by an operator to support continuous forward or reverse winding (scrolling) of the tape 506, where the rotational speed of the associated motor is controlled by the potentiometer 810.

Each resistor 806 includes any suitable resistive structure having any suitable resistance. Each transistor 808 includes any suitable switching device that selectively creates a current path. In this example, each transistor 808 represents an n-channel enhancement MOSFET device, although other types of transistors could be used. Each potentiometer 810 includes any suitable structure providing a variable resistance. Each pushbutton 812 includes any suitable structure that selectively creates a current path based on manual depression.

The controller 210 also includes a pushbutton trigger 814, a pulse circuit 816, and a toggle switch 818. The pushbutton trigger 814 allows an operator to trigger pulsed rotation of one of the motors 108-110, where the pulse is created by the pulse circuit 816 and the toggle switch 818 controls which motor 108-110 is rotated. The width of the pulse is adjustable as described above to compensate for factors such as different reel sizes or component pitches. Ideally, the width of the pulse causes one of the motors 108-110 to rotate by an amount that moves a new component into an imaging position for inspection.

The pushbutton trigger 814 includes a resistor 820 and a pushbutton 822. The resistor 820 includes any suitable resistive structure having any suitable resistance. The pushbutton 822 includes any suitable structure that selectively creates a current path based on manual depression. The toggle switch 818 includes any suitable structure for selectively controlling where an input signal is output.

The pulse circuit 816 includes any suitable structure for creating electrical pulses. In some embodiments, the pulse circuit 816 is implemented using an LM555 timer from TEXAS INSTRUMENTS. This or other type of timer could generate a pulse lasting a defined period of time in response to a trigger input. The length of the pulse is adjustable using a potentiometer 824 and capacitors 826-828. The potentiometer 824 includes any suitable structure providing a variable resistance. Each capacitor 826-828 includes any suitable capacitive structure having any suitable capacitance.

The transistors 808 of the drive circuits 802-804 are driven by the pulse circuit 816 via the toggle switch 818. Thus, in response to depression of the pushbutton 822, the pulse circuit 816 generates a pulse for moving the tape 506, ideally by an amount necessary to move one component out of an imaging position and to move another component into the imaging position. The toggle switch 818 controls whether the transistor 808 in the drive circuit 802 or the transistor 808 in the drive circuit 804 receives the pulse, thereby controlling whether the motor 108 or the motor 110 rotates.

Although FIG. 8 illustrates one example of a controller 210 for a system that supports reel-to-reel inspection of semiconductor devices or other components, various changes may be made to FIG. 8. For example, while the use of pushbuttons is shown, various other types of devices could be used to selectively control operation of the system 200. Also, the internal structures of the components 802, 804, 814, 816 are for illustration only and can vary depending on how those components are implemented.

Figure 9:
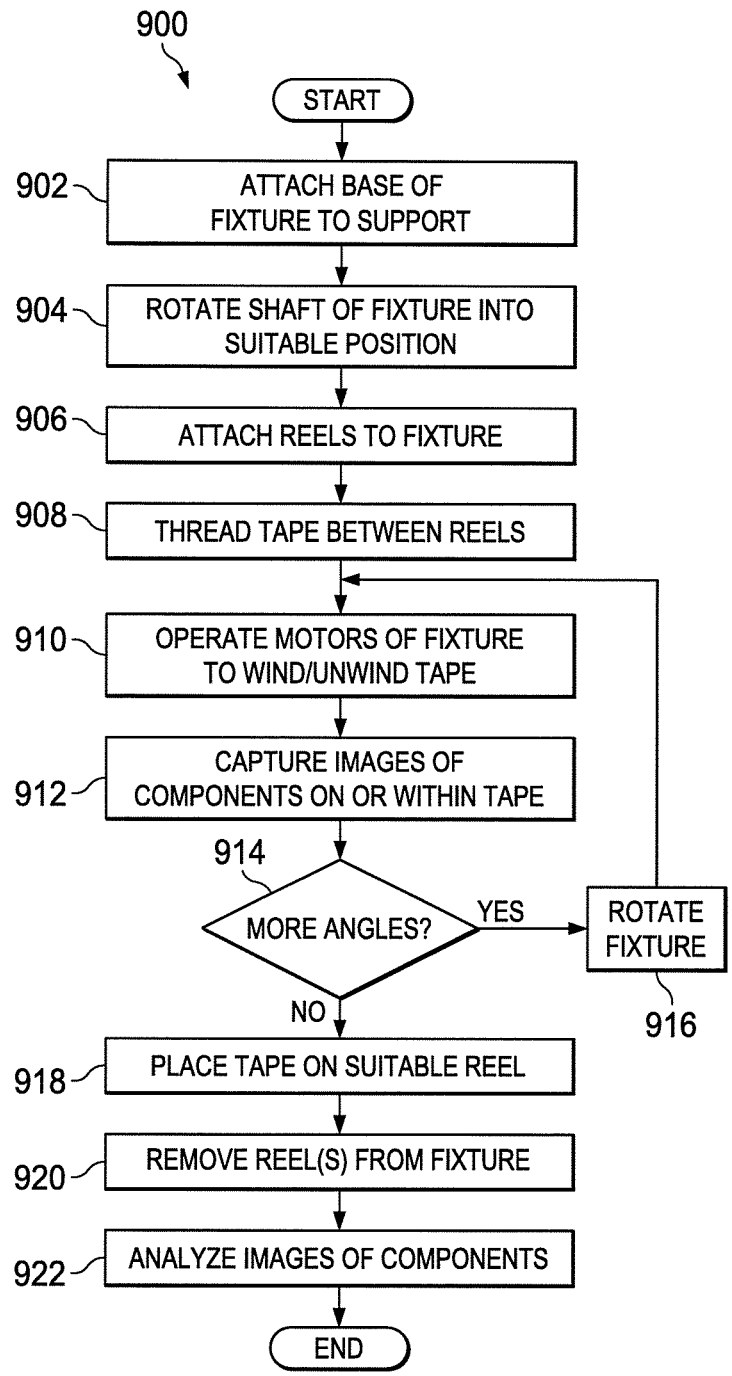
FIG. 9 illustrates an example method for supporting reel-to-reel inspection of semiconductor devices or other components using a fixture in accordance with this disclosure.

FIG. 9 illustrates an example method 900 for supporting reel-to-reel inspection of semiconductor devices or other components using a fixture in accordance with this disclosure. For ease of explanation, the method 900 is described with respect to the fixture 100 of FIG. 1 being used in the system 200 of FIGS. 2 through 7. However, the method 900 could involve any other suitable fixture or any other suitable system.

As shown in FIG. 9, a base of a fixture is attached to a support at step 902. This could include, for example, personnel coupling the base 102 of the fixture 100 to a table or other support using bolts or other connectors. The support could form a part of or be located near an inspection system. A shaft of the fixture is rotated into a suitable position at step 904. This could include, for example, the personnel using the pivot joint 106 to rotate the shaft 104 of the fixture 100 into a position where a tape 506 can pass through an imaging position of the inspection system.

Reels are attached to the fixture at step 906. This could include, for example, the personnel attaching the reels 502-504 to axles or other projections of the motors 108-110. One of the reels can include a tape 506 having components to be inspected, and the other reel could be empty. The tape is threaded between the reels at step 908. This could include, for example, the personnel extending the tape 506 from the reel 502 and attaching an end of the tape 506 to the reel 504.

The components carried in or on the tape are inspected by operating motors of the fixture to wind/unwind the tape at step 910 and by capturing images of the components at step 912. This could include, for example, the controller 210 operating (automatically or based on manual input) to generate pulses that cause the motor 108 or 110 to advance the tape 506 by an amount necessary to image each component. This could also include the radiation source 202 generating continuous or intermittent radiation so that the radiation detector 204 can capture one or more images of each component being inspected. A determination is made whether images of the components at another angle are needed at step 914. If so, the fixture is rotated at step 916. This could include, for example, the personnel using the pivot joint 106 to rotate the shaft 104 about the longitudinal axis of the shaft 104, which allows the components to be imaged again at a different angle.

Otherwise, if necessary, the tape is placed onto a suitable reel at step 918. In some embodiments, the tape 506 is initially located on one of the reels 502 or 504, and the tape 506 needs to be returned to the same reel 502 or 504 after the inspection in completed. If the tape 506 is not located on the desired reel, the personnel could use the controller 210 to wind the tape 506 onto the desired reel. At least one reel is removed from the fixture at step 920. This could include, for example, the personnel removing the reel on which the tape 506 is wound from the fixture 100. The other reel could optionally remain on the fixture 100 for use during inspection of additional components.

The captured images are analyzed (either in real-time or at a later time) at step 922. There are various techniques for analyzing X-ray or other images of semiconductor devices or other components. For example, in some techniques, X-ray images of semiconductor devices are compared to one another or to X-ray images of known good components in an attempt to determine whether certain semiconductor devices are counterfeit. However, any of a wide variety of other analyses could occur.

Although FIG. 9 illustrates one example of a method 900 for supporting reel-to-reel inspection of semiconductor devices or other components using a fixture, various changes may be made to FIG. 9. For example, while various steps were described above as being performed manually, one, some, or all of those operations could be performed in an automated manner. Also, while shown as a series of steps, various steps in each figure could overlap, occur in parallel, occur in a different order, or occur any number of times. As a particular example, the shaft of the fixture may need to be rotated into a suitable position after the reels are attached to the shaft and the tape is threaded between the reels, and the shaft may need to be rotated again after imaging in order to allow removal of the reel(s).

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
a fixture configured to receive multiple reels that are each configured to receive a tape in or on which components to be inspected are located;
wherein the fixture comprises:
a base configured to be secured to a support;
a shaft;
one or more motors mounted to the shaft and configured to rotate the reels; and
one or more joints coupling the shaft and the base, wherein the one or more joints are configured to allow (i) rotation of the shaft about a longitudinal axis of the shaft to change an orientation of the shaft with respect to the base and (ii) rotation of the shaft to change a direction at which the shaft extends away from the base such that the tape is movable into and out of a path of radiation that is generated by a radiation source.

2. The apparatus of claim 1, wherein:
the base is configured to be secured to different supports of different component inspection systems; and
the one or more joints are configured to allow positioning of the shaft in different positions depending on configurations of the different component inspection systems.

3. The apparatus of claim 1, further comprising:
a controller configured to drive the one or more motors.

4. The apparatus of claim 1, wherein the fixture further comprises:
at least one additional motor configured to reorient and reposition the shaft.

5. The apparatus of claim 1, wherein the base is configured to be removably secured to the support such that the base is removable from a first component inspection system and securable to a second component inspection system having a different configuration from the first component inspection system.

6. The apparatus of claim 1, wherein the shaft extends linearly from the one or more joints such that the one or more motors are located distally along the shaft from the one or more joints.

7. The apparatus of claim 2, wherein the one or more joints are configured to allow positioning of the shaft horizontally in a first component inspection system and vertically in a second component inspection system.

8. The apparatus of claim 3, wherein:
the one or more motors comprise a first motor and a second motor; and
the controller comprises:
a first drive circuit configured to control operation of the first motor; and
a second drive circuit configured to control operation of the second motor.

9. The apparatus of claim 8, wherein:
the first drive circuit comprises a first transistor having a first gate;
the second drive circuit comprises a second transistor having a second gate; and
the controller further comprises:
a pulse circuit configured to generate pulses in response to trigger inputs; and
a switch configured to selectively direct the pulses to the first and second gates.

10. The apparatus of claim 9, wherein the controller further comprises a control configured to adjust widths of the pulses.

11. The apparatus of claim 9, wherein each of the first and second drive circuits further comprises:
a control configured to cause scrolling of the tape; and
a control configured to adjust a speed of the scrolling.

12. A system comprising:
a component inspection system comprising:
a radiation source configured to generate radiation; and
a radiation detector configured to detect the radiation after the radiation passes through components to be inspected; and
a fixture configured to receive multiple reels that are each configured to receive a tape in or on which the components are located;
wherein the fixture comprises:
a base configured to be secured to a support;
a shaft;
one or more motors mounted to the shaft and configured to rotate the reels; and
one or more joints coupling the shaft and the base, wherein the one or more joints are configured to allow (i) rotation of the shaft about a longitudinal axis of the shaft to change an orientation of the shaft with respect to the base and (ii) rotation of the shaft to change a direction at which the shaft extends away from the base such that the tape is movable into and out of a path of the radiation that is generated by the radiation source and detected by the radiation detector.

13. The system of claim 12, wherein the one or more joints are configured to allow positioning of the shaft horizontally or vertically depending on an arrangement of the radiation source and the radiation detector in the component inspection system.

14. The system of claim 12, further comprising:
a controller configured to drive the one or more motors.

15. The system of claim 12, wherein the one or more joints are configured to allow rotation of the shaft about the longitudinal axis of the shaft so that the component inspection system is able to capture images of the components at multiple angles.

16. The system of claim 14, wherein:
the one or more motors comprise a first motor and a second motor; and
the controller comprises:
a first drive circuit configured to control operation of the first motor; and
a second drive circuit configured to control operation of the second motor.

17. The system of claim 16, wherein:
the first drive circuit comprises a first transistor having a first gate;
the second drive circuit comprises a second transistor having a second gate; and the controller further comprises:
- a pulse circuit configured to generate pulses in response to trigger inputs; and
- a switch configured to selectively direct the pulses to the first and second gates.

18. The system of claim 17, wherein the controller further comprises a control configured to adjust widths of the pulses.

19. The system of claim 17, wherein each of the first and second drive circuits further comprises:
- a control configured to cause scrolling of the tape; and
- a control configured to adjust a speed of the scrolling.

20. The system of claim 18, wherein the control is configured to adjust the widths of the pulses to account for variations in (i) sizes of the reels and (ii) a pitch between components in or on the tape.

21. A method comprising:
- securing a base of a fixture to a support;
- placing a shaft of the fixture into a specified location, wherein one or more joints couple the shaft and the base and one or more motors are mounted to the shaft;
- coupling multiple reels to the one or more motors, each reel configured to receive a tape in or on which components to be inspected are located; and
- controlling winding and unwinding of the tape to and from the reels to allow a component inspection system to capture one or more images of each component;

wherein the one or more joints are configured to allow (i) rotation of the shaft about a longitudinal axis of the shaft to change an orientation of the shaft with respect to the base and (ii) rotation of the shaft to change a direction at which the shaft extends away from the base such that the tape is movable into and out of a path of radiation that is generated by a radiation source of the component inspection system.

22. The method of claim 21, wherein:
- the base is configured to be secured to different supports of different component inspection systems; and
- the one or more joints are configured to allow positioning of the shaft in different positions depending on configurations of the different component inspection systems.

23. The method of claim 21, wherein:
- the one or more motors comprise a first motor and a second motor; and
- controlling the winding and unwinding of the tape to and from the reels comprises generating pulses to control operation of the first and second motors, the pulses having adjustable widths to account for variations in (i) sizes of the reels and (ii) a pitch between components in or on the tape.

* * * * *